(12) United States Patent
Doguet et al.

(10) Patent No.: US 11,052,260 B2
(45) Date of Patent: Jul. 6, 2021

(54) IMPLANTABLE ELECTRODE COUPLED TO AN OPTOELECTRONIC DEVICE

(71) Applicant: Synergia Medical, Mont-Saint-Guibert (BE)

(72) Inventors: Pascal Doguet, Mont-Saint-Guibert (BE); Marie Dautrebande, Mont-Saint-Guibert (BE); Carmen Godfraind, Mont-Saint-Guibert (BE)

(73) Assignee: SYNERGIA MEDICAL, Mont-Saint-Guibert (BE)

( * ) Notice: Subject to any disclaimer, the term of this patent is extended or adjusted under 35 U.S.C. 154(b) by 0 days.

(21) Appl. No.: 16/634,598

(22) PCT Filed: Aug. 31, 2017

(86) PCT No.: PCT/EP2017/071858
§ 371 (c)(1),
(2) Date: Jan. 28, 2020

(87) PCT Pub. No.: WO2019/042553
PCT Pub. Date: Mar. 7, 2019

(65) Prior Publication Data
US 2020/0206514 A1    Jul. 2, 2020

(51) Int. Cl.
*A61N 1/37* (2006.01)
*A61N 1/378* (2006.01)
(Continued)

(52) U.S. Cl.
CPC ............... *A61N 1/378* (2013.01); *A61B 5/24* (2021.01); *A61B 5/6846* (2013.01);
(Continued)

(58) Field of Classification Search
CPC .... A61N 1/378; A61N 1/0534; A61N 1/0556; A61B 2562/0209
See application file for complete search history.

(56) References Cited

U.S. PATENT DOCUMENTS 5,454,837 A * 10/1995 Lindegren ............... A61N 1/05
607/9
6,711,440 B2 * 3/2004 Deal ....................... A61N 1/372
607/9

(Continued)

FOREIGN PATENT DOCUMENTS

| EP | 0377547 A1 | 7/1990 |
| WO | 2016/131492 A1 | 8/2016 |
| WO | 2017/004576 A1 | 1/2017 |

OTHER PUBLICATIONS

Int'l. Search Report for PCT/EP2017/071858, dated Oct. 13, 2017.

*Primary Examiner* — Eric D. Bertram
(74) *Attorney, Agent, or Firm* — Blue Filament Law PLLC

(57) ABSTRACT

An optoelectronic electrode element includes an electrode module (40) having at least a first and second electrodes (41, 42) each having an electrode surface (41s, 42s). An an optoelectronic module (20) is provided and having a photovoltaic cell (21a) suitable for transforming optical energy into electrical energy. A feeding fibre optic (31a) is also provided. A coupling module (10) is provided and having a circuit receiving portion (12) for inserting, positioning, and rigidly fixing the optoelectronic module (20) to the coupling module (10); and a feeding fibre cavity (11a) for inserting and coupling the feeding fibre optic to bring it in optimal optical communication with the photovoltaic cell. The coupling module (10) is coupled directly to a fixing area of the electrode module (40), such that the photovoltaic cell be in electrical contact with the first and second electrodes (41, 42).

18 Claims, 7 Drawing Sheets

(51) Int. Cl.
  *A61B 5/00* (2006.01)
  *A61N 1/05* (2006.01)
  *A61B 5/24* (2021.01)

(52) U.S. Cl.
  CPC .............. *A61B 2560/0219* (2013.01); *A61B 2562/0209* (2013.01); *A61N 1/0534* (2013.01); *A61N 1/0556* (2013.01)

(56) References Cited

U.S. PATENT DOCUMENTS

| | | | |
|---|---|---|---|
| 6,829,509 | B1 | 12/2004 | MacDonald |
| 6,988,001 | B2 * | 1/2006 | Greatbatch ............ A61N 1/056 607/37 |
| 8,632,577 | B1 * | 1/2014 | Bendett ................ A61N 5/0603 607/88 |
| 8,744,568 | B2 * | 6/2014 | Weber .................. A61N 1/3787 604/20 |
| 10,350,424 | B2 * | 7/2019 | Doguet .............. A61N 1/36125 |
| 2002/0116033 | A1 * | 8/2002 | Greatbatch ........ A61N 1/37512 607/33 |
| 2002/0133216 | A1 * | 9/2002 | Connelly .............. A61N 1/056 607/116 |
| 2003/0204207 | A1 * | 10/2003 | MacDonald ......... A61N 1/3752 607/2 |
| 2005/0070987 | A1 * | 3/2005 | Erickson ................ A61N 1/05 607/122 |
| 2005/0268962 | A1 * | 12/2005 | Gaudiana ............... H02S 30/20 136/255 |
| 2007/0043404 | A1 * | 2/2007 | Deimling ............ A61N 1/0534 607/61 |
| 2019/0168022 | A1 * | 6/2019 | Doguet ............. A61N 1/36125 |

* cited by examiner

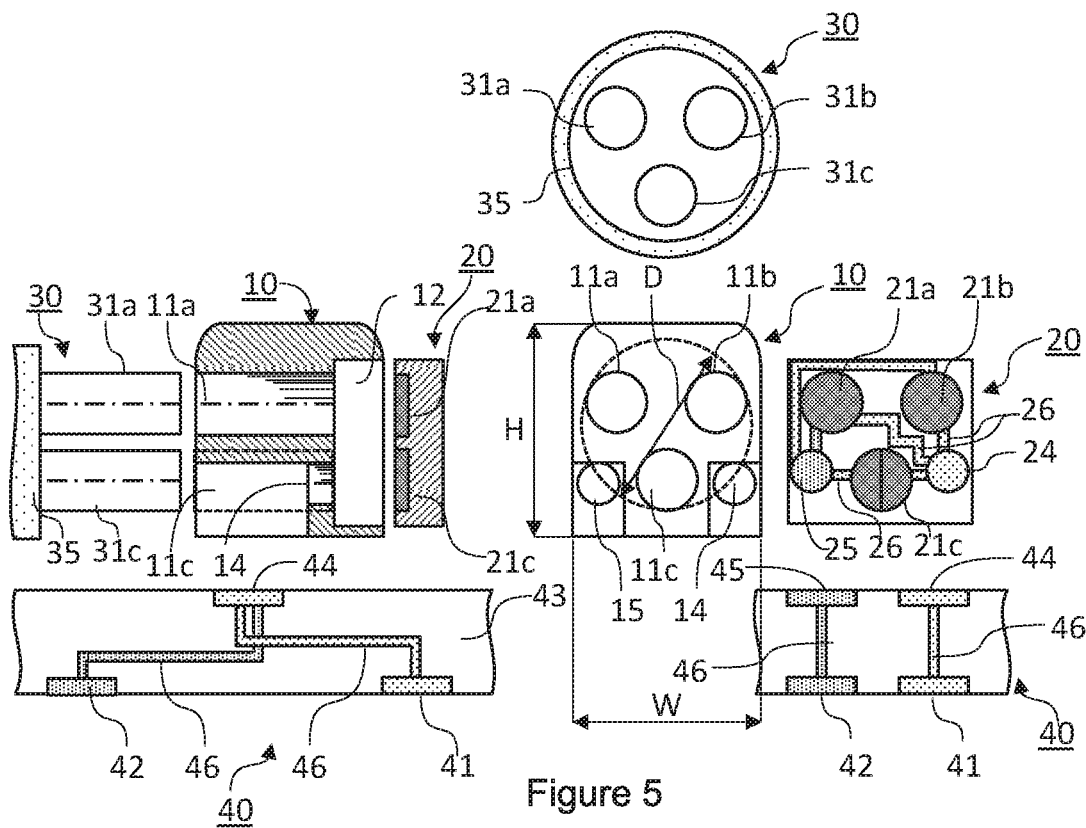
Figure 5
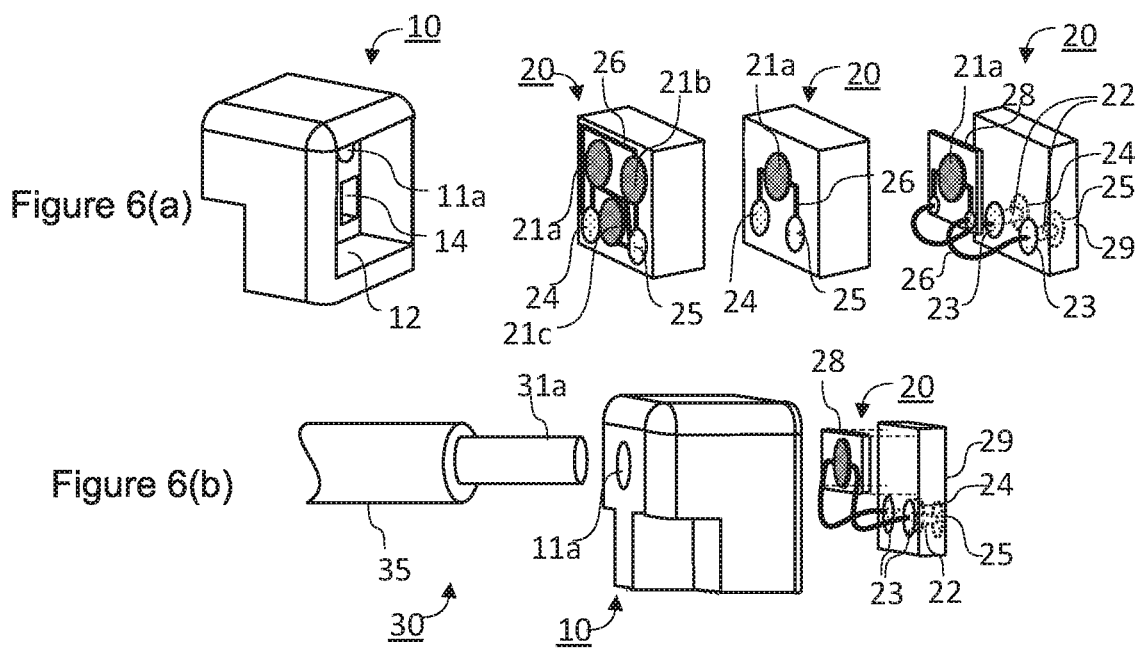
Figure 6(a)
Figure 6(b)

IMPLANTABLE ELECTRODE COUPLED TO AN OPTOELECTRONIC DEVICE

TECHNICAL FIELD

The present invention concerns an implantable medical device (IMD) for use in a medical treatment involving the transmission of light through a fibre optic, between a housing of the IMD and an electrode module, which is coupled to a biological tissue. In particular, the present invention addresses an optoelectronic electrode element comprising an electrode module, an optoelectronic module comprising an optoelectronic device (e.g., a photovoltaic cell or a source of light), a fibre optic, and a coupling module for bringing the foregoing modules together and forming a solid, yet compact and efficient continuous optical energy transmission chain between the fibre optic and the electrode module. An optoelectronic device comprised within the optoelectronic module can be either an optical-to-electrical transducer such as a photovoltaic cell, a photodiode, a photo-resistor, an optical switch and the like, or an electrical-to-optical transducer, i.e, a light source such as a LED, a laser diode. The optoelectronic electrode element of the present invention is modular, allowing a great design flexibility, which can be adapted to all kinds of electrodes.

BACKGROUND OF THE INVENTION

Implantable medical devices (IMD) have been used for decades for treating a number of disorders, in particular neurological disorders. A major type of IMD's consists of neurostimulators, which deliver electrical pulses to a tissue such as a nerve or a muscle for diagnosing or treating a number of disorders such as Parkinson's disease, epilepsy, chronic pain, motor disorders, and many other applications. In its simplest form, a device for delivering such electrical pulses comprises an electrical pulse generator lodged in a housing, stimulating electrodes and electric leads electrically coupling the electrodes to the electrical pulse generator. In many applications, the electrodes must be applied directly onto the tissue to be treated, requiring the use of an implantable device. The electric wires simply end forming electrodes, generally partially embedded in an electrically insulating support which geometry depends on the type of treatment the IMD is designed for.

Rather than conducting electrical current from a housing of an IMD containing the pulse generator, electronic controller and power source, through electrical conductors to electrodes fixed to a target nerve, muscle or any other tissue, several applications have been developed using light to transfer energy from an IMD housing to the electrodes through fibre optics. An example is described in WO2016131492A1. The light energy is transformed into electric current by photovoltaic cells, said current being directly delivered to electrodes for stimulating the tissue to be treated.

In alternative applications, light can also be used to transfer information from an IMD housing to the electrodes through a second feeding fibre optic. An IMD can for example comprise, on the one hand, a photovoltaic cell receiving light by means of a first feeding fibre optic to power an optoelectronic circuit and, on the other hand, a second feeding fibre optic conveying digital or analog information used to generate stimulation waveforms to be fed to the electrodes.

In yet alternative applications, monitoring vital functions, neural signals or other physiological parameters can be performed by transferring light signals from a tissue to the IMD housing by means of a feedback fibre optic. The light signals may be generated by a voltage sensitive light emitting element. The light emitting element can be coupled to an optoelectronic circuit, powered by a photovoltaic cell (as discussed supra) and amplifying, processing and converting the captured signal into a suitable light emission signal to be fed into the same fibre optic as, or a different fibre optic from the one coupled to the photovoltaic cell.

The design of an assembly formed by one or more fibre optics, an optoelectronic module, and electrodes, hereinafter referred to as "optoelectronic electrode element," is more complex than with traditional IMD's using electric leads. This is because several components must be assembled in perfect alignment in as small a volume as possible, to reduce the size of the optoelectronic electrode element. Indeed, a poor alignment of the components of the optoelectronic electrode element increases the intensity losses of transferred optical signal. This is particularly sensitive for photovoltaic cells energized through a feeding fibre optic as a low efficacy of energy transfer from the fibre optic to the electrodes limits the autonomy of the IMD.

US20070043404 describes an IMD comprising a light source, a fibre optic transmitting light energy to a photovoltaic cell coupled to electrodes. The photovoltaic cell is planar and flexible, such that it can be wrapped around an end of a fibre optic. The photovoltaic cell and the end of the fibre optic are disposed in a protective housing into which the fibre optic enters and out of which the electrode tips leave. The light reaching the end of the fibre optic is deflected out of the axis of the fibre optic towards the photovoltaic cell wrapped around it by small mirror constructions or prism constructions or by cauterizing or breaking the fibre optic end so as to scatter the light in a diffused fashion. The deflection of the light beam is complex and generates substantial losses of energy transfer from the fibre optic to the photovoltaic cell.

US20050070987A1 describes an IMD comprising several electrodes coupled to a generator by an electric lead, passing by optically activated switches. The optically activated switches are optically connected to a light source by means of a corresponding number of fibre optics. The transmission of light through a fibre optic activates the corresponding optical switch which allows passage of electrical current from the leads to the corresponding electrodes. In an alternative embodiment, the electric wire is eliminated and the optical switches are replaced by photovoltaic cells, which are electrically coupled to corresponding electrodes. US20050070987A1 describes only the principles of the arrangement of the optoelectronic electrode element, but fails to give any actual construction details.

Because IMD's must be miniaturized, only small sources of energy are used, limiting their autonomy. A rechargeable battery can be used, of course, but loading a battery blocks the host of the IMD and prevents him from any non-static activity during the time required for the loading. An example of recharging device is described, e.g., in PCT/EP2016/061722. It follows that energy cannot be wasted and the transfer of light from an emitter to a receiver must be as energy-effective as possible.

Another issue with IMD's is their longevity. In order to avoid having to replace an implanted medical device, it is desired that the service life time of an IMD be as long as possible. One major cause of failures of IMD's is infiltration of alien pollutants through degraded joints. Another possible cause of failure is reduction or disruption of the transfer of optical energy from the fibre optic to the photovoltaic cell, which can be due to a misalignment of the fibre optic with respect to the optoelectronic device, or breakage of the fibre optic, in particular close to the connecting region with the optoelectronic device.

The present invention proposes an IMD comprising an optoelectronic electrode element having a versatile design adaptable to various types of electrodes, which is very compact, ensures a long term structural stability, and yields a highly efficient energy transfer chain between the fibre optic and electrodes. These and other advantages are described in more details in the following sections.

SUMMARY OF THE INVENTION

The present invention is defined in the appended independent claims. Preferred embodiments are defined in the dependent claims. In particular, the present invention concerns an optoelectronic electrode element which is implantable in a human or animal body for placement on a biological tissue for electrically stimulating and/or sensing physiological parameters of said biological tissue, said optoelectronic electrode element comprising:
  (a) an electrode module comprising:
    an electrically insulating support for coupling the implantable electrode element to a biological tissue, wherein said insulating support comprises an electrode coupling surface (43s) and partly embeds;
    at least a first and second electrodes each comprising an electrode surface, which are separated from one another and exposed to ambient atmosphere at the respective electrode surfaces, such that when the optoelectronic electrode element is coupled to a biological tissue, the first and second electrode surfaces are in electrical contact with the biological tissue, and
    a first and second coupling surfaces in electrical communication with the first and second electrodes, respectively,
  (b) an optoelectronic module comprising an optoelectronic circuit including one or more optoelectronic devices suitable for transforming optical energy into electrical energy and/or electrical energy into optical energy, said optoelectronic module further comprising a first and second optoelectronic module contact surfaces in electrical communication with the optoelectronic circuit,
  (c) an optical module comprising one or more fibre optics, each having a distal end characterized by a cross-section of hydraulic diameter, Dh, said distal end being in optical communication with a corresponding optoelectronic device,
  (d) a coupling module comprising:
    a circuit receiving portion for inserting, positioning, and rigidly fixing the optoelectronic module to the coupling module;
    one or more fibre cavities; each one for inserting and coupling the distal end of a corresponding fibre optic such that the cross-section of the distal end is in optical communication with, and faces in accurate alignment with the corresponding optoelectronic device;
  (e) wherein, the coupling module is coupled directly to a fixing area of the electrically insulating support, and wherein the first and second optoelectronic module contact surfaces are distinct from and in electrical contact with the first and second coupling surfaces of the electrode module, respectively.

The optoelectronic electrode element of the present invention has the advantage of being solid and of small dimensions. In particular, it is preferred that each of the one or more fibre cavities of the coupling module extends substantially parallel to a support vector, z, and are all enclosed within a circle of diameter, D, normal to the support vector, z. A projection of the coupling module onto a plane normal to the support vector, z, has a surface having a first dimension, H, of preferably not more than 300%, more preferably not more than 200%, most preferably not more than 100% of the diameter, D. Said surface has a second dimension, W, normal to the first dimension which is preferably not more than 300%, preferably not more than 200%, more preferably not more than 100% of the diameter, D. In terms of absolute values, the first and/or second dimensions, H, W, are preferably smaller than 5 mm, more preferably smaller than 3 mm.

In a preferred embodiment, the one or more optoelectronic devices comprise a photovoltaic cell, whose corresponding fibre optic is a feeding fibre optic, and wherein the first and second optoelectronic module contact surfaces are in electrical communication with and electrically fed by the photovoltaic cell.

Additionally, or alternatively, the one or more optoelectronic devices may comprise a light emitting device, whose corresponding fibre optic is a feedback fibre optic, said light emitting device having an optical output which:
  (a) is representative of the activity of an optoelectronic device suitable for transforming optical energy into electrical energy and/or
  (b) can be modulated by variations of an electrical potential difference between the first and second electrode surfaces of the electrode module.

In the latter case, the optoelectronic circuit may compris an amplification chain for amplifying the variations of the electrical potential difference between the first and second electrodes of the electrode module, said amplification chain being powered by a photovoltaic cell of the optoelectronic module.

A good electric communication between the optoelectronic circuit and the first and second electrodes is essential. This is achieved by electrically bridging the first and second optoelectronic module contact surfaces with the first and second coupling surfaces of the electrode module, respectively, by means of one or more of,
  a conductive paste comprising a conductive polymer, a polymer loaded with conductive particles, or a low melting temperature metal,
  a conductor selected among a conductive wire or ribbon, a printed circuit or track, wherein said conductor is bonded at a first end to the first or second optoelectronic module contact surface) and, at a second end to the corresponding first or second coupling surface, wherein bonding can be formed by one or more of wire bonding, ribbon bonding, wire or ribbon laser welding, soldering.
  direct contact of the first or second optoelectronic module contact surface with the corresponding first or second coupling surface, and welding, riveting, clamping, snap fitting, with a plug and socket assembly, soldering with a conductive soldering material the surfaces in contact, or by simple contact between planar surfaces.

In order to enhance imperviousness of the optoelectronic electrode element of the present invention against any biological fluids, it is preferred that the whole coupling module be embedded in an insulating polymer. The insulating polymer can be silicone, an epoxy resin, a poly(p- xylylene) polymer, liquid crystal polymer or mixture or multi-layered laminate thereof. This has the advantages of stabilizing the coupling module on the insulating support, of insulating the coupling module from the surrounding environment, and of smoothening any sharp edge or corner of the coupling module. If the one or more fibre optics, excluding the distal ends thereof, are enclosed in a sheath, then the insulating polymer preferably continuously embeds the distal ends and part of the sheath.

In order to protect the optoelectronic circuit from contacting any biological fluid when implanted, each of the one or more optoelectronic devices can be separated from the distal end of the corresponding fibre optic by a corresponding window transparent to the wavelength transmitted to or from the corresponding fibre optic. The corresponding windows can be an integral part of the coupling module, wherein the coupling module is made of a transparent ceramic material forming a monolithic block including the corresponding windows. The transparent ceramic material is preferably selected from: fused silica, borosilicate, spinel, sapphire, or yttrium oxide.

In a preferred embodiment, a coupling assembly formed by the optoelectronic module and the coupling module is formed as follows:
  (a) the circuit receiving portion is formed by a circuit cavity,
  (b) the optoelectronic circuit is supported on a support board defining a support board perimeter mating or overlapping the circuit cavity,
  (c) the optoelectronic module is inserted in or over the circuit cavity forming a support interfacial perimeter between the support board perimeter and the coupling module,
  (d) the support interfacial perimeter is sealed with a sealing element preferably selected among a welding such as Femtosecond laser welding, or soldering line, or a sealing polymer (27) applied to the main interfacial perimeter.

Alternatively, the coupling assembly can be formed as follows:
  (a) the circuit receiving portion is formed by a circuit cavity,
  (b) the optoelectronic circuit is supported on a support board defining a support board perimeter mating or smaller than the circuit cavity,
  (c) The support board is coupled to a first surface of a main board, defining a main board perimeter, mating or overlapping the circuit cavity,
  (d) the optoelectronic module is inserted in or over the circuit cavity forming a main interfacial perimeter between the main board perimeter and the coupling module,
  (e) the main interfacial perimeter is sealed with a sealing element preferably selected among a welding such as Femtosecond laser welding, or soldering line, or a sealing polymer applied to the main interfacial perimeter, and wherein
  (f) the first and second optoelectronic module contact surfaces (24, 25) are located on a second surface of the main board, separated from the first surface of the main board, and wherein the electrical communication between the optoelectronic circuit and the first and second optoelectronic module contact surfaces (24, 25) is ensured by vias, extending across the thickness from the first to the second surface of the main board In a preferred configuration, the one or more optoelectronic devices comprise:

(a) A first photovoltaic cell, whose corresponding fibre optic is a first feeding fibre optic, wherein said first photovoltaic cell is arranged for feeding electrical power to a stimulating circuit including the first and second electrodes, for transporting charges in a first direction to stimulate a tissue,
  (b) A second photovoltaic cell, whose corresponding fibre optic is a second feeding fibre optic, which can be the same as or different from the first feeding fibre optic, wherein said second photovoltaic cell is arranged for feeding electrical power to a recovery circuit including the first and second electrodes, for transporting charges in a second direction, opposite the first direction, to balance the charges delivered by the stimulation circuit,
  (c) One or more sources of light, including a LED or a laser diode included in the stimulation circuit and/or the recovery circuit, whose corresponding fibre optics are one or more feedback fibre optics, wherein said one or more sources of light are powered by the first and/or second photovoltaic cells, and whose output is optionally modulated by variations of an electrical potential measured between the first and second electrodes.

Sealing of the optoelectronic circuit from ambient atmosphere can be achieved by one or more of the following:
  (a) the optoelectronic circuit is enclosed in a circuit cavity provided in the coupling module, and an interface formed between the optoelectronic module and the coupling module is sealed by a sealing element,
  (b) the one or more fibre cavities are closed at one end by a window (18) transparent to the wavelengths transported through the fibre optics, and separating the fibre cavities from the circuit cavity,
  (c) all electrical communications between a first surface and a second surface of a wall of a non-conductive component is formed by vias made of conductive metals extending from the first to the second surfaces of the wall, and preferably a coating of conductive metal is applied over the vias where they reach the first and second surfaces.

The present invention also concerns an implantable medical device comprising:
  (a) a housing comprising one or more sources of light and a controller, and
  (b) an optoelectronic electrode element as described above, comprising one or more photovoltaic cells, and one or more corresponding fibre optics,
  (c) wherein the one or more sources of light of the housing are in optical communication with the one or more photovoltaic cells through the one or more fibre optics. The electrode module is preferably shaped as a cuff or helical ribbon suitable for being fitted around a nerve, a needle or rod suitable for being inserted in a brain tissue, a two-dimensional array suitable for being laid over the cerebral cortex or on the spinal cord.

BRIEF DESCRIPTION OF THE FIGURES

For a fuller understanding of the nature of the present invention, reference is made to the following detailed description taken in conjunction with the accompanying drawings in which.

FIG. 5: shows cut views of an embodiment according to the present invention of optoelectronic electrode elements applied to cuff electrodes comprising feeding fibre optics and feedback fibre optics aligned with corresponding photovoltaic cells and light emitting device.

FIGS. 6(a) and 6(b): show different perspective views of examples of a coupling module and optoelectronic modules.

FIG. 8(b) a stimulating circuit according to the present invention coupled to a recovery circuit.

DETAILED DESCRIPTION OF THE INVENTION

Figure 1:
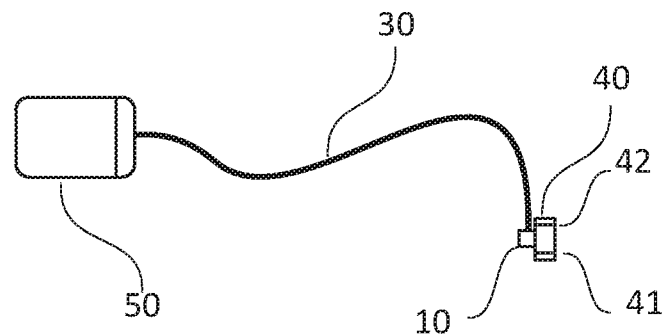
FIG. 1: shows an IMD according to the present invention.

As illustrated in FIG. 1, an implantable medical device (IMD) according to the present invention comprises a housing (50) containing the electronics for controlling the functions of the IMD, including for example a light emitting source and a source of power, generally in the form of a primary or rechargeable battery. An optoelectronic electrode element (40) comprises at least first and second electrodes (41, 42) and can be coupled to a tissue to be treated. Treatment may include, on the one hand, stimulation of a tissue by application of electrical voltage or current pulses through the tissue comprised between the two electrodes and/or, on the other hand, recording of electrical signals measured between the two electrodes. For stimulation of a tissue, the current is supplied to the electrodes by means of a photovoltaic cell powered by a light emitting source located in the housing whose light is transmitted to the photovoltaic cell through a feeding fibre optic (31a). A light emitting source located in the housing (the same or different as the previous one) can also be used to power an optoelectronic circuit located in the optoelectronic electrode element and comprising a light source, e.g. a LED, which output may be modulated by potential variations between the electrodes representative of the activity of the treated tissue. The light source output can be transmitted to the housing through a feedback fibre optic (31c) which can be the same as or different from the foregoing feeding fibre optic.

Because the housing is usually too bulky to be implanted adjacent to the tissue to be treated, it is generally implanted in an easy to access region, remote from the tissue to be treated and from the optoelectronic electrode element. When the optoelectronic device includes a photovoltaic cell, optical energy is transferred from the light emitting source of the housing to the photovoltaic cell through at least one feeding fibre optic (31a).

An optoelectronic electrode element is more complex than a conventional electrical electrode element, wherein electric current is transferred from and/or to the housing directly to and/or from the electrodes through electric wires. The electric energy transfer chain between the battery of the housing and the electrodes is easily achieved with wires, and feedthroughs. By contrast, in the case of an optoelectronic IMD comprising a photovoltaic cell, optical energy is transferred through a feeding fibre optic (31a) from a light emitting source in the housing to a photovoltaic cell (21a), whence it is converted into electrical energy, providing direct electric current between the electrodes or powering the optoelectronic module. The energy transfer chain from the housing to the electrodes involves the conversion by a photovoltaic cell of light energy emitted by a light emitting source located in the housing into electric energy at the electrode. The efficacy of the energy transfer and energy conversion in photovoltaic IMD's is of prime importance, and yet seldom addressed in the literature. In some cases, the photovoltaic cell and optoelectronic module associated therewith are housed in a second housing located close to but separate from the electrode module, coupled thereto by electric leads. The photovoltaic cell and optoelectronic module associated therewith are generally housed separately from the electrodes because to date these elements are too bulky to be integrated directly to an electrode element. Requiring a second housing close to albeit separate from the electrodes increases the overall bulkiness of the optoelectronic electrode element, rendering it more complex to implant, and thus considerably neutralizes the advantages of wireless optoelectronic IMD's discussed supra. The present invention proposes a compact and resistant optoelectronic electrode element ensuring optimal light to electrical and electrical to light energy conversions, which is easy to produce and to adapt to any type of electrode types used in the art, and which is reliable over long periods after implanting into a patient.

Figure 2A:
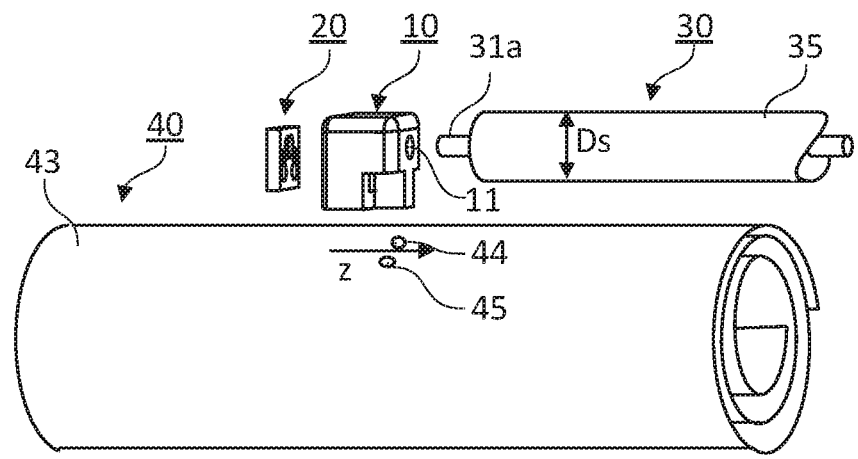
FIGS. 2(*a*) and 2(*b*): show an example of optoelectronic electrode element according to the present invention, with the electrode module forming a cuff electrode FIG. 2(*a*) exploded view, and FIG. 2(*b*) assembled view.

An optoelectronic electrode element according to the present invention is implantable in a human or animal body for placement on a biological tissue for electrically stimulating and/or sensing physiological parameters of said biological tissue. It can be powered by a source of light energy. As shown in FIG. 2, an optoelectronic electrode element according to the present invention is modular and comprises:

an electrode module (40),
an optical module (30),
an optoelectronic module (20), and
a coupling module (10).

The modular nature of the optoelectronic electrode element of the present invention affords a great freedom for adapting it to any types and sizes of electrodes. Stimulation as well as recording functions can easily be implemented without losing any of the advantages cited above.

Electrode Module (40)

The electrode module (40) comprises an electrically insulating support (43) for coupling the implantable electrode element to a biological tissue. The geometry of the support depends on the specific application of the IMD. For example, the electrode module can be in the shape of cuff or helical ribbon electrode to be wrapped around a target nerve (cf. e.g., FIGS. 2(a) and (b) & FIGS. 7(a)-(e)), a rod or needle for deep brain stimulation treatments (cf. FIGS. 4(a)-(g)), a two-dimensional array, and the like, all well known in the art. The insulating support comprises an electrode coupling surface (43s), which may contact the tissue to be treated without any effect thereon. The insulating support is used for securing the electrodes at their treatment positions for long term implantation. The insulating support is preferably made of a polymeric material. If the insulating material must be deformed for insertion and for accommodating any body movement, it is preferably made of an elastomeric polymer, such as silicone or a polyurethane elastomer. For other electrodes geometries, such as deep brain stimulation electrodes, the insulating support can be rigid and made for example of polyurethane or of an epoxy resin.

The electrode module further comprises at least a first and second electrodes (41, 42) at least partially embedded in the insulating support, such as to expose electrode surfaces (41s, 42s) adjacent to the electrode coupling surface (43s). The at least first and second electrodes are separated from one another. When the optoelectronic electrode element is coupled to a biological tissue, the first and second electrode surfaces (41s, 42s) are in electrical contact with the biological tissue. The first and second electrodes (41, 42) are in electrical communication with a first and second coupling surfaces (44, 45), respectively. The electrical communication between electrodes and coupling surfaces can be established with leads, or printed tracks, preferably embedded in the insulating support. The materials used for the electrodes, coupling surfaces and electric communication are not restricted by the present invention, and any known electric conducting material suitable for implantable applications can be used, such as gold, platinum, platinum-iridium alloys, and conducting polymers.

The electrode module can be bipolar and comprise two electrodes charged positively and negatively (+, −) when activated. Alternatively, it can be tripolar and comprise three electrodes charged for example negatively, positively, and negatively (+, −, +). All the electrodes with same polarity are electrically coupled to a corresponding same first or second coupling surface. One coupling surface (44, 45) can therefore be coupled to more than one electrode. More electrodes may be assembled in series or in parallel.

Inversely, one electrode can be coupled to more than one source of energy, through corresponding more than one coupling surfaces. This can be useful if one pair of electrodes needs to be powered more than a second pair of electrodes.

Optoelectronic Module (20)

The optoelectronic module (20) comprises an optoelectronic circuit supported on a support board (28), which can be rigid or flexible. The support board can optionally be coupled to a main board (29) (cf. FIGS., 6(*a*) right, and 7(*d*)). This can be advantageous for the choice of materials if a specific geometry or property is required, which is difficult yield with support boards generally available on the market.

The optoelectronic circuit includes one or more optoelectronic devices. The one or more optoelectronic devices can include optical-to-electrical transducers (O-E), such as a photovoltaic cell (21a) suitable for transforming optical energy into electrical energy, which can be injected directly into the electrodes. Such O-E-transducers can serve for feeding electrical power to a stimulating and/or a recovery circuit including the first and second electrodes, for transporting charges in a first and/or a second direction to stimulate a tissue.

Alternatively, or additionally, the one or more optoelectronic devices can include electrical-to-optical transducers (E-O) (=light emitting sources) such as photodiodes, LEDs, laser diodes, photo-resistors, optical switches, which can be powered by one such photovoltaic cell. Such E-O-transducers can be directly powered by an O-E-transducer or used to translate electrical signals outputted by an electronic sensing circuit powered by the photovoltaic cell.

The optoelectronic module further comprises a first and second optoelectronic module contact surfaces (24, 25) in electrical communication with the optoelectronic circuit and, in particular, with the photovoltaic cell (21a) from which they can be fed in electrical current. The optoelectronic circuit is preferably a photonic integrated circuit customized for the specific intended uses. It can also integrate on the same Soc (system-on-chip) optical elements such as a photovoltaic cell and a so called ASIC (=application-specific integrated circuit). Modern ASICs often include entire microprocessors, memory blocks including ROM, RAM, EEPROM, flash memory and other large building blocks. For example, silicon photonic devices can be made using existing semiconductor fabrication techniques, and because silicon is already used as the substrate for most integrated circuits, it is possible to create hybrid devices in which the optical and electronic components are integrated on a single microchip.

The first and second optoelectronic module contact surfaces (24, 25) can be arranged on a second surface different from a first surface of the support board on which the optoelectronic circuit is supported. For example, the second surface can be the surface of the support board which is opposite to the first surface of the support board. Alternatively, the second surface can be a surface of a main board (29) opposite a coupling surface of the main board which is coupled to the support board. In such cases, it is preferred that the electrical communication between the optoelectronic devices and the first and second optoelectronic module contact surfaces (24, 25) be created by vias (22). Vias are rods made of a noble, conductive metal, such as Au, Pt, Ir, Pd, Ni, Cu, Ti, or W, or alloys thereof, which are inserted across the thickness of a wall thus forming a conductive bridge between a first and second surface of said wall. The use of vias is advantageous in the present applications because they are fluid tight. The area surrounding and including the ends of a via, which are flushed with the first and second surfaces of the wall it traverses can be coated with a layer (23) of conductive metal, preferably selected among the same materials as the via, to form larger contact areas which can easily be coupled to conductors by wire bonding or the like. The coated layers applied on the second surface can form the first and second optoelectronic module contact surfaces (24, 25).

As discussed more in detail below, the one or more optoelectronic devices of the optoelectronic circuit may for example include a light emitting device (21c)—typically a LED—, which is in electrical communication with the first and second coupling surfaces (44, 45) and with the first and second electrodes (41, 42) of the electrode module. The light emitting device can be powered by the photovoltaic cell (21a). In some applications, the optical output may be modulated by variations of an electrical potential difference measured in the tissue between the first and second electrode surfaces (41q, 42s) of the electrode module. By transmitting the modulated signal emitted by the light emitting device (21c) through a feedback fibre optic (31c) to the electronics contained in the housing (50), data on the tissue can thus be collected and analysed. The optoelectronic circuit may also comprise a photovoltaic cell (21a, 21b) for powering an amplification and signal processing chain. Variations of electrical potential differences measured between the first and second electrode surfaces of the electrode module can thus be amplified, processed, and converted into a suitable light emission signal.

Figure 8A:
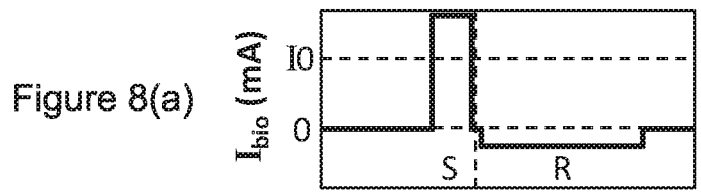
FIGS. 8(a) and 8(b): show FIG. 8(a) a stimulating pulse followed by a recovery pulse.
Figure 8B:
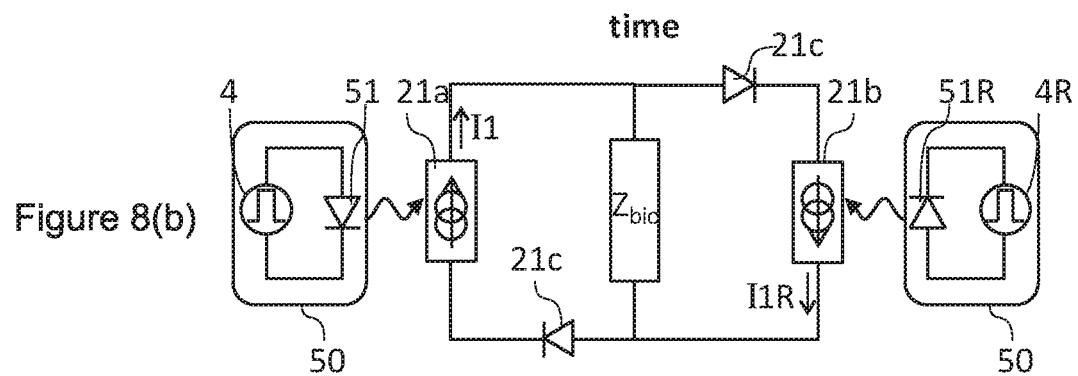

As discussed above, the optoelectronic devices may comprise at least a first photovoltaic cell (21a), which is powered by light energy transmitted through a first feeding fibre optic (31a) facing said first feeding fibre optic (31a), and which is arranged for feeding electrical power to a tissue comprised between the first and second electrodes, through a stimulating circuit. The charges delivered to a tissue must, however, be recovered, lest irreversible electrochemical changes would take place. For this reason, it is preferred that the electrical circuit including the electrodes be made bipolar, i.e., that current can circulate in both directions. The stimulation circuit transports charges in a first direction to stimulate the tissue, and an electric charge recovery circuit is formed transporting charges in the opposite direction. This process is illustrated in FIG. 8(a) showing an electrical stimulating pulse (S) of intensity higher than a threshold tissue stimulating intensity (10), followed by a balanced charge recovery pulse (R) of intensity lower than the threshold tissue stimulating intensity, which should ideally have the same current×time area as the stimulating pulse. An example of recovery circuit is illustrated in FIG. 8(b). The portion of circuit located on the left-hand side of the tissue ($Z_{bio}$) to be treated is the stimulating circuit as discussed above. The circuit on the right-hand side of the tissue ($Z_{bio}$) is the recovery circuit mounted in parallel with the stimulating circuit, and only differing from the latter in that the direction of the current, I1R, is inverted with respect to the current, I1, of the stimulating circuit. The electrical charge recovery circuit is fed by a second photovoltaic cell (21b) powered by light energy transmitted through a second feeding fibre optic (31b) facing said second feeding fibre optic (31b). The stimulating circuit and recovery circuit are meant to be activated sequentially, not simultaneously. Other embodiments of recovery circuits are discussed more in details in [0035]&[0036] of WO2016131492, which contents is herein incorporated by reference, and can be used in the present invention.

As illustrated in FIG. 8(b), one or more sources of light (21c), including a LED or a laser diode can be included in the stimulation circuit and/or the recovery circuit. The one or more sources of light face one or more feedback fibre optics (31c), which transmit the light emitted by the sources to a controller in the housing (50), wherein said one or more sources of light are powered by the first and/or second photovoltaic cells. In an embodiment, the light emitted by the one or more sources of light (21c) is a control means to ensure that current is flowing correctly in the stimulating or recovery circuit, and that the IMD functions correctly. In an alternative embodiment, the output of the one or more sources of light, powered by the first or second photovoltaic cell (21a, 21b) can be modulated by variations of an electrical potential measured between the first and second electrodes, revealing an activity of the treated tissue.

Optical Module (30)

The optical module (30) comprises one or more fibre optics (31a-c), characterized by a cross-section of hydraulic diameter, Dh. Generally, the cross-section of a fibre optic is circular of diameter, Do. If the optoelectronic device is a photovoltaic cell, the corresponding fibre optic is a feeding fibre optic (31a) having, on the one hand, a proximal end in optical communication with a light emitting source lodged in the housing (50) of the IMD and, on the other hand, a distal end in optical communication with the photovoltaic cell (21a) of the optoelectronic module. The hydraulic diameter, Dh, of the cross-section of a fibre is defined as, Dh=4 A/P, wherein A is the area, and P the perimeter of the cross-section. If the cross-section is circular, the hydraulic diameter is the diameter, Do, of the circle, Dh=Do.

As illustrated in FIG. 5, the optical module (30) may comprise more than one fibre optic. For example, it may comprise more than one feeding fibre optic (31a, 31 b), wherein a feeding fibre optic is herein defined as a fibre optic transmitting light energy from a light emitting source lodged in the housing towards the optoelectronic electrode element. The housing may comprise more than one light emitting sources, optically coupled to corresponding feeding fibre optics or to a single feeding fibre optic. The optical module may also comprise one or more feedback fibre optics (31c). A feedback fibre optic is herein defined as a fibre optic transmitting light energy from the optoelectronic electrode element towards the housing.

A fibre optic is not defined by a direction of light transmission, and a same fibre optic can be used as feeding or as feedback fibre optic. It is the position of the fibre optic facing a light source at its proximal or at its distal end which defines herein whether a fibre optic is a feeding or a feedback fibre optic. If a light emitting source is positioned in concentric alignment with a photovoltaic cell or with a photodetector, a single fibre optic can be used both as feeding and as feedback fibre optic.

As well known in the art, a fibre optic comprises one or more cores enclosed in a cladding, wherein the refractive index of the cladding must be lower than the refractive index of the core, to constrain the light emission within the core. Core and cladding can be made of a mineral glass or of a polymeric material, often referred to as "Polymer Optical Fibre" (POF). A fibre optic (31a-c) is preferably enclosed within a polymeric sheath (35), to protect it mechanically as well as from contact with moisture from the external environment. A sheath (35) is particularly useful when the optical module (30) comprises more than one fibre optic (31a-c), as illustrated in FIG. 5. The sheath (35) is defined by a cross-section having a hydraulic diameter, Ds, and it preferably comprises one or more lumens for accommodating a corresponding number of fibre optics. Each fibre optic can thus be introduced or withdrawn from a corresponding lumen. Alternatively, the sheath can also be overmoulded around the fibre optics. The sheath is preferably made of a polymeric elastomer, having low friction with, on the one hand, the surfaces of the fibre optics and, on the other hand, with surrounding tissues it may contact between the housing and the photovoltaic element when implanted. For example, the sheath can be made of silicone, polyurethane, polycarbonate, Carbothane™ and the like.

Coupling Module (10)

The gist of the present invention is the coupling module, which allows coupling all the foregoing modules to form an efficient energy transmission chain between the feeding or feedback fibre optic and the optoelectronic module, with a transformation of optical energy into electric energy and/or of electrical energy into optical energy. Examples of coupling modules according to the present invention are illustrated in FIGS. 2 to 7.

Figure 3A:
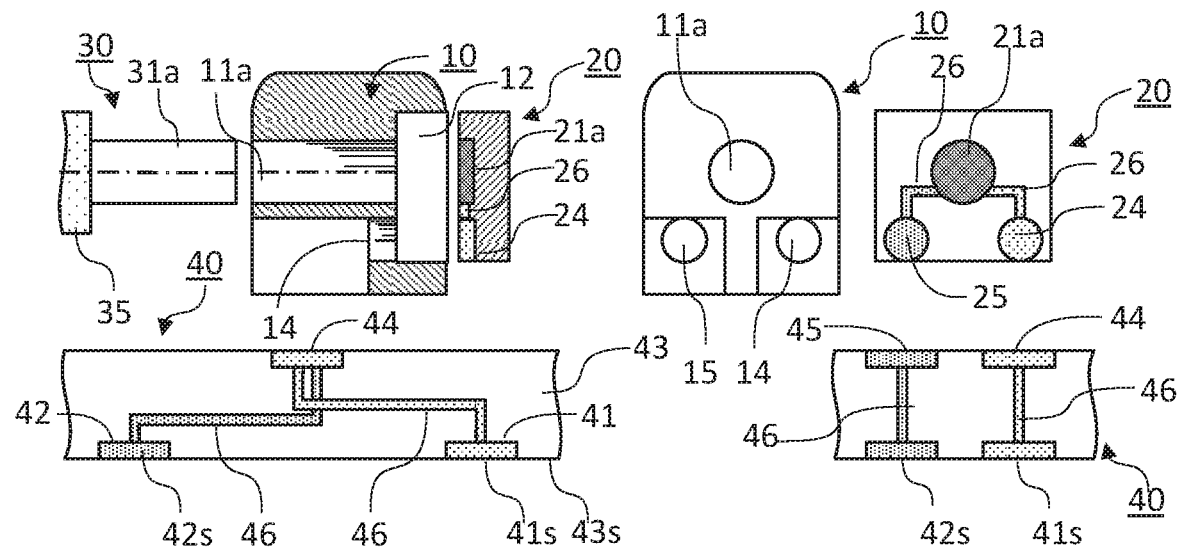
FIGS. 3(a) and 3(b): show cut views of two embodiments according to the present invention of optoelectronic electrode elements applied to cuff electrodes.

The coupling module (10) comprises a circuit receiving portion (12) for positioning, and rigidly fixing the support board (28) or the main board (29) of the electronic module (20) to the coupling module (10). The accurate positioning of the electronic module with respect to the coupling module is of paramount importance for the efficacy of the energy transfer chain, as it will determine the degree of alignment of the optoelectronic device (21a-21c) with the corresponding fibre optic (31a-c). The optoelectronic device which is most sensitive to the degree of alignment is without doubt a photovoltaic cell (21a) with a corresponding feeding fibre optic (31a). If the receiving portion is a cavity as illustrated in FIGS. 3(a), 4(b), and 6(a), it can be accurately machined, or etched, to tolerances of the order of ±50 µm, preferably ±20 µm by methods well known in the art.

The coupling module (10) also comprises one or more fibre cavities (11a-c) for inserting and coupling the distal end of corresponding one or more fibre optics (31a-c) such that the cross-section of the distal end of each fibre optic is in optical communication with, and faces in accurate alignment a corresponding optoelectronic device (21a-c). Here again, the one or more fibre cavities (11a-c) can be machined or etched with a high accuracy within tolerances of the order of ±10-20 µm by methods well known in the art. Again, the accurate positioning of the one or more fibre optics with respect to the corresponding one or more optoelectronic devices (21a-c) of the electronic module (20) is of paramount importance for the efficacy of the energy transfer chain.

FIG. 5 illustrates an optoelectronic electrode element comprising
  (a) A first photovoltaic cell (21a), facing a first feeding fibre optic (31a). The first photovoltaic cell is arranged for supplying electrical current to the first and second electrodes through a stimulating circuit (cf. FIG. 8(b)).
  (b) A second photovoltaic cell (21b), facing a second feeding fibre optic (31b). The second photovoltaic cell is arranged for supplying electrical current to the first and second electrodes through a recovery circuit (cf. FIG. 8(b)).
  (c) A first and second sources of light (21c), such as LEDs or laser diodes, represented in FIG. 5 as a single device split in two sources of light, both facing a feedback fibre optic (31c). The first and second sources of light can be arranged in the stimulating and recovery circuits and are powered by the first and second photovoltaic cells, respectively. The light emitted by said first or second sources of light can be representative of current flowing through the stimulating or recovery circuit, indicating the proper functioning of the circuits. Optionally, the intensity of light emitted by the source of light can be modulated by variations of an electrical potential measured between the first and second electrodes.

The one or more fibre cavities (11a-c) can be in fluid communication with the circuit receiving portion (12), in alignment with the corresponding photovoltaic cell(s) (21a, 21b) and/or light sources (21c). If the electronic module is sensitive to moisture, windows (18) transparent to the wavelength of the transmitted light can separate the corresponding fibre cavities (11a-c) from the circuit receiving portion (12). The windows can be separate windows fixed to a distal end of the corresponding fibre optic cavity (11a-c) of the coupling module or, alternatively, the windows can be an integral part of the coupling module which must thus be made of a material transparent to the light wavelength. The coupling module can thus be made of a transparent ceramic material forming a monolithic block including the corresponding windows, which is selected from: fused silica, borosilicate, spinel, sapphire, or yttrium oxide.

Assembly of the Various Modules to Form an Optoelectronic Electrode Element

The optoelectronic electrode element of the present invention is formed by the assembly of the foregoing modules as follows.

Coupling assembly(=(10)+(20))

Figure 7A:
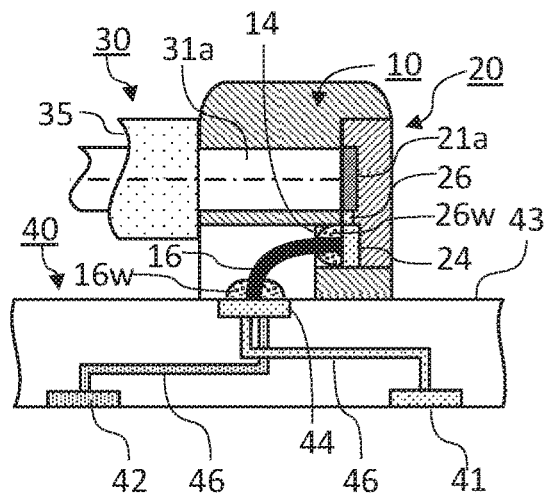
FIGS. 7(a)-7(e): show different cut views of assembled optoelectronic electrode elements according to the present invention.

The optoelectronic module (20) is coupled in accurate alignment to the coupling module (10) to form a coupling assembly, such that optoelectronic devices, such as the one or more optoelectronic devices (21a-c), must be in perfect alignment with corresponding fibre optic cavities (11a-c). The optoelectronic module (20) can be coupled to the coupling module (10) by any means known in the art, including gluing, welding, soldering, fusion bonding, snap fitting, and the like. A sealing element can be added to seal from an outside of the coupling module the electronic module, at least the optoelectronic circuit thereof, within the circuit receiving portion. In case the circuit receiving portion is formed by a circuit cavity the sealing element can be a lid welded to a perimeter of the circuit cavity. The lid can be formed by the support board (28) supporting the optoelectronic circuit. Alternatively, the lid can be formed by a main board (29) comprising a first main surface to which the support board (28) is coupled (cf. FIGS. 4A, 6(a) (right), 6(b), and 7(d)). A sealing polymer (27), such as a biocompatible epoxy, can be applied over an interface between such lid and the coupling module, such as at the edges of the circuit cavity, as illustrated in FIG. 7(e). This operation is made in plant.

The optoelectronic module can be sealingly coupled to a circuit receiving portion (12) formed by a circuit cavity, by inserting the optoelectronic module in or over the circuit cavity forming an interfacial perimeter between an optoelectronic module perimeter and the coupling module. The interfacial perimeter can then be sealed with a sealing element preferably selected among a welding or soldering line, or a sealing polymer (27) applied to the interfacial perimeter. Because the dimensions of the optoelectronic module are so small, and in order to protect the optoelectronic circuit during welding, Femtosecond laser welding is preferred for sealing the interfacial perimeter. As discussed supra, if the lid is formed by the support board (28), then a support interfacial perimeter is formed between the coupling module and the support board (28), and can be sealed. In case the support board is fixed to a surface of a main board (29) then a main interfacial perimeter is formed between the coupling module and the main board (29), and can be sealed.

In a particularly advantageous embodiment of the present invention, the optoelectronic circuit is sealed from ambient atmosphere surrounding the coupling assembly. This is, of course, of paramount importance for the longevity of the optopelectronic circuit when implanted. But sealing the optoelectronic circuit within the coupling assembly has the further advantage of facilitating any handling thereof during manufacturing, without fear of contaminating or allowing moisture to contact the optoelectronic circuit. Examples of sealed coupling assemblies are illustrated in FIG. 7(c)&(d). First, the optoelectronic module can be sealingly coupled to the coupling module, as explained supra. If necessary, a sealing polymer (27) can be applied to further seal the interface between the optoelectronic and the coupling modules. Second, the fibre optics cavities (11a-c) can be closed at one end by a window (18) physically isolating the fibre optics cavities from the circuit cavity, and thus from the optoelectronic circuit. Third, any electric communication across a wall is formed by vias (22) extending from one surface to another across a thickness of the wall, forming a conductive bridge across the wall. As shown in FIG. 7(c), vias can replace the openings (14) shown in FIGS. 3(a), 5 and 6(a) (left). As shown in FIG. 7(d) vias can be used for forming an electrical communication across a lid formed by the support board (28) or, as illustrated in FIG. 7(d), by a main board (29) to which the support board is bonded. This way, a coupling assembly can be produced under controlled conditions in plant, with no risk of contamination or moisture corrosion of any internal surface of the assembly and, in particular, of the optoelectronic circuit.

Electrode assembly(=(10)+(20)+(40))

The coupling assembly formed by the coupling module (10) and the optoelectronic module (20) can be fixed to the electrode module (40) to form an electrode assembly. The coupling assembly must have a fixing area suitable for forming a fixing interface with a fixing area of the insulating support. Fixing the coupling assembly to the electrode module can be performed by any means known in the art. For example, it can be bonded with an adhesive, by welding, soldering, fusion bonding, and the like. It can also be fixed by mechanical means, including screws, rivets, snap fittings, clamping, and the like. The fixing of the coupling assembly to the electrode module must include the establishment of an electrical contact between the first and second electronic module contact surfaces (24, 25) of the electronic module (20) with the corresponding first and second coupling surfaces (44, 45) of the electrode module (40).

Depending on the geometry of the optoelectronic electrode element, additional conductive means for bringing the first and second electronic module contact surfaces (24, 25) in electric contact with the corresponding first and second coupling surfaces (44, 45) of the electrode module, may or may not be required. In embodiments illustrated in FIGS. 3(b) and 4(e)-(g), no additional conductive means are required to establish an electrical contact between the electronic module contact surfaces (24, 25) and the coupling surfaces (44, 45). This is possible if, for example, on the one hand, the first and second electronic module contact surfaces (24, 25) belong to the fixing area of the coupling assembly and, on the other hand, the first and second coupling surfaces (44, 45) belong to the fixing area of the electrode module. By forming a fixing interface between the coupling assembly and the electrode module, the electronic module contact surfaces (24, 25) can be brought at the same time in direct electric contact with the coupling surfaces (44, 45) of the electrode module.

Figure 3B:
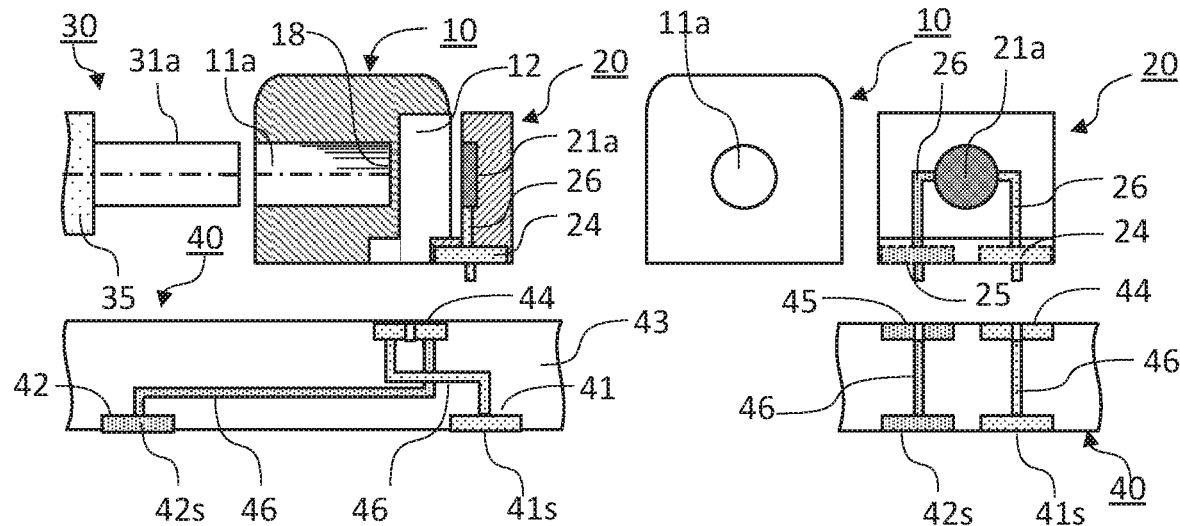

In particular, FIG. 3(b) represents an optoelectronic electrode element in the form of a cuff electrode, wherein the electronic module contact surfaces (24, 25) after assembly of the electronic module (20) with the coupling module (10) belong to the fixing area which is to be brought into contact with the electrode module upon fixing the coupling assembly thereto. As illustrated in FIG. 3(b), pins may be provided, which snugly fit corresponding cavities to form a plug and socket assembly between the electronic module contact surfaces (24, 25) and coupling surfaces (44, 45). Such arrangement can be advantageous to ensure an optimal electrical contact between the electronic module and the electrodes (41, 42). For thinner assemblies, a good electrical contact can also be achieved without pins and sockets, by simple contact of planar electronic module contact surfaces (24, 25) with planar coupling surfaces (44, 45).

Figure 4A:
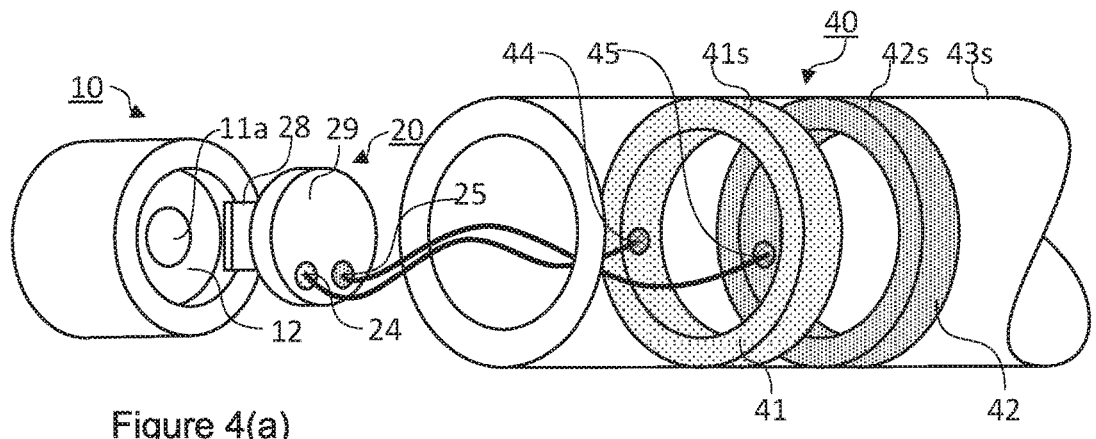
FIGS. 4(a)-4(d): show FIG. 4(a) exploded perspective views, FIG. 4b) exploded cut views, FIG. 4(c) assembled cut views of an embodiment according to the present invention of modules of an optoelectronic electrode element in the form of deep brain stimulation electrodes, and FIG. 4(d) general view.
Figure 4B:
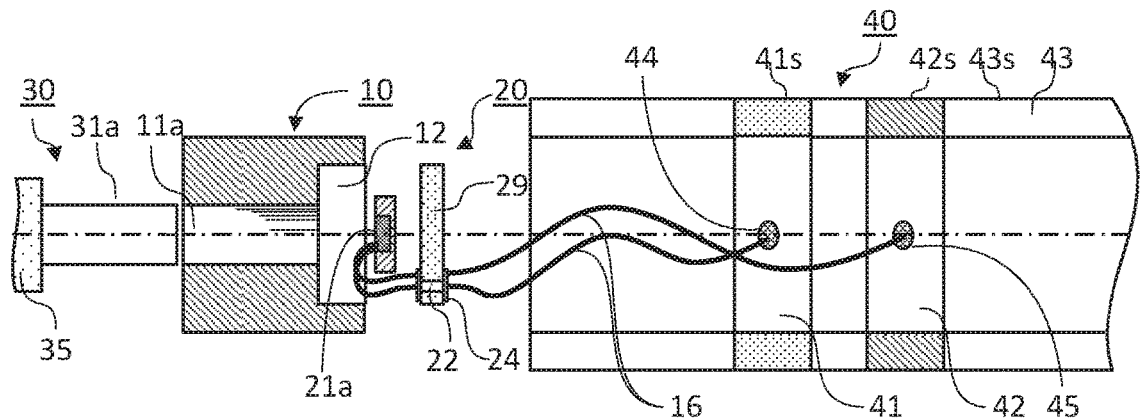
Figure 4C:
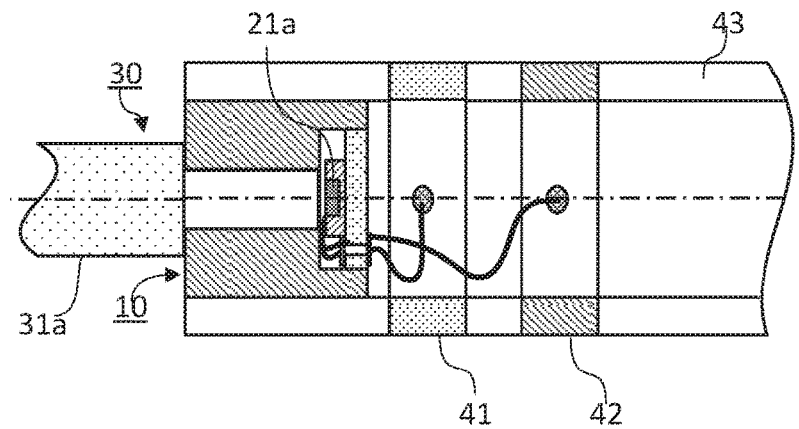

FIGS. 4A&4B represent two embodiments of an optoelectronic electrode element in the form of a deep brain stimulation electrode, wherein the electronic module contact surfaces (24, 25) are, on the one hand, in the form of conductive layers coated over vias (22) illustrated in FIG. 4A and, on the other hand, in the form of circular grooves, illustrated in FIG. 4B. The cylindrical coupling assembly can be inserted into a cylindrical cavity, filled with a first and second (and more) electrodes (41, 42) with corresponding coupling surfaces (44, 45). The coupling surfaces of the electrodes illustrated in FIG. 4A are formed by any surface of the electrodes, suitable for binding a conductive wire to the electronic module contact surfaces (24, 25) and to the corresponding coupling surfaces (44, 45). The coupling surfaces of the electrodes illustrated in FIG. 4B are in the form of hollow cylinders jutting out in the direction of the axis of the cylindrical electrode module. By inserting the coupling assembly to the electrode module of FIG. 4B, the first and second coupling surfaces engage into the grooves of the first and second optoelectronic module contact surfaces (24, 25). The optoelectronic module contact surfaces (24, 25) need not be in the form of circular grooves, and can be in the form of simple openings for receiving corresponding pins. If the corresponding contact surfaces are not concentric with the axis of the cylindrical electrode module, the coupling module and electrode module may comprise guiding means for setting the angular orientation of the coupling assembly with respect to the electrode module. For example, a system of flange and channel could be used to this effect.

In another embodiment, the electrical contact between the first and second electronic module contact surfaces (24, 25) of the electronic module (20) and the corresponding first and second coupling surfaces (44, 45) of the electrode module (40) requires electrically bridging the surfaces with an additional conductive material. This embodiment is illustrated in FIG. 7(a)&(b). In FIG. 7(a), one or more conductor elements (16) selected among for example a conductive wire or ribbon, a printed circuit or track, or a metal foil, or an electrical connector, such as, but not limited to a spring-loaded connector is used to electrically bridge the electronic module contact surfaces (24, 25) with the corresponding coupling surfaces (44, 45). The conductor element (16) can be bonded at a first end to an electronic module contact surface (24, 25) and, at a second end to the corresponding coupling surface (44, 45), by any known technique, such as by wire bonding, ribbon bonding, spot welding, soldering, conductive adhesive and the like.

Figure 7B:
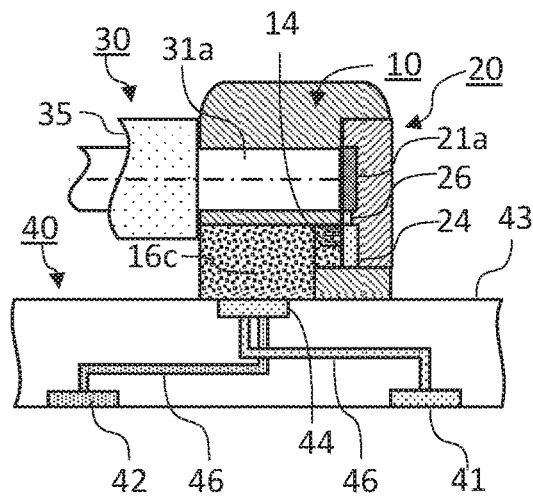
Figure 7C:
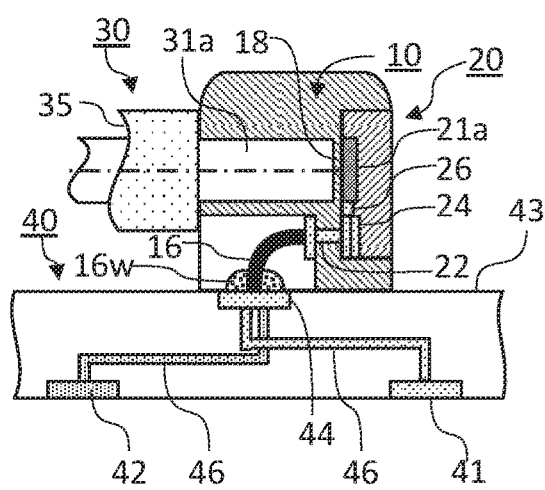
Figure 7D:
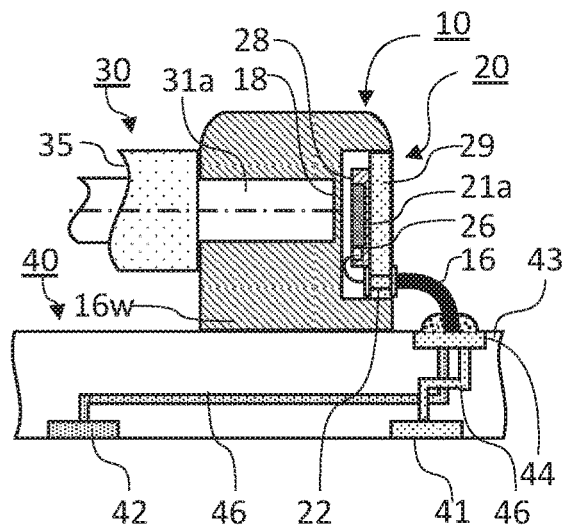
Figure 7E:
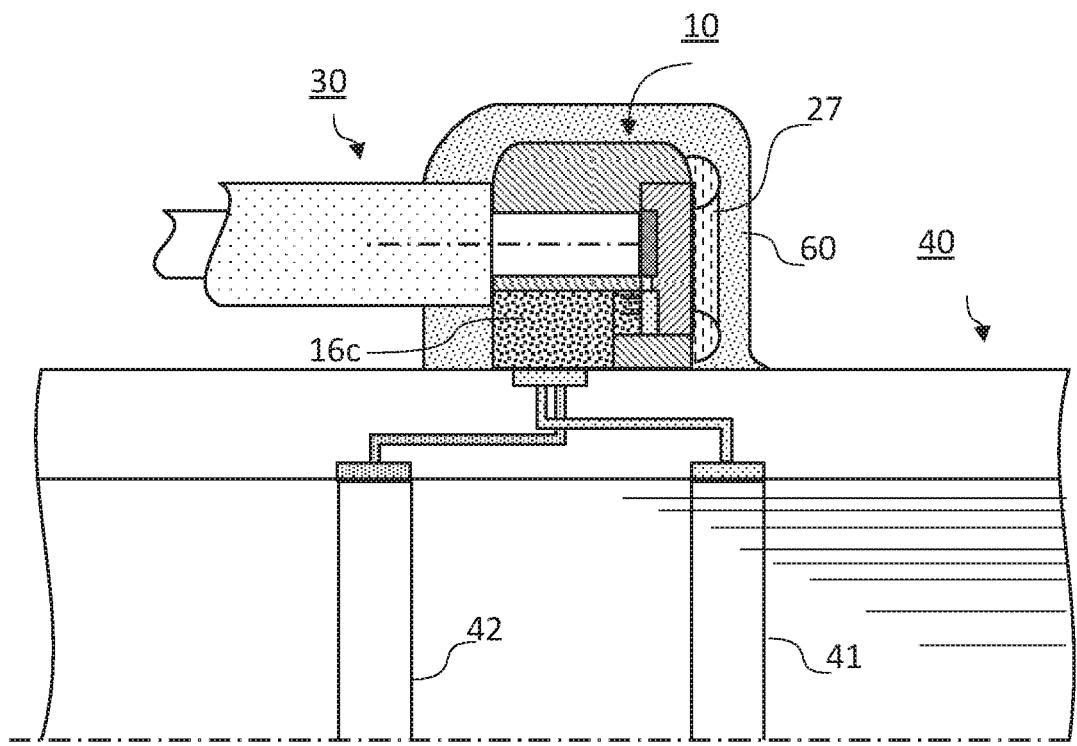

In FIG. 7(b), a conductive paste (16c) comprising a conductive polymer or a polymer loaded with conductive particles is used to electrically bridge the electronic module contact surfaces (24, 25) with the corresponding coupling surfaces (44, 45).

In the embodiments of FIG. 7(a)&(b), openings (14) are provided in the coupling module for giving access from the outside to the electronic module contact surfaces (24, 25) (cf. also FIGS. 3(a)&6(a)). After assembly of the various modules to form an optoelectronic electrode element according to the present invention, such openings are preferably sealed, e.g., with an epoxy, a silicone, or the like, to prevent any short-circuiting when implanted. The use of vias (22) was discussed supra with respect to FIGS. 7(c)&(d).

Optical assembly(=(10)+(30))

An optical module (30) as discussed supra can be coupled to the coupling module (10) to form an optical assembly. If the coupling module is already coupled with the optoelectronic and the electrode assemblies, an optoelectronic electrode element of the present invention is formed. The one or more fibre optics (31a-c) of the optical module (40) are preferably enclosed in a sheath (35) of hydraulic diameter, Ds. The distal ends of each of the one or more fibre optics juts out of the sheath, and can be inserted into the corresponding, snugly fitting fibre optic cavities (11a-c) of the coupling module. The geometry of the end surfaces of the fibre optics must be carefully controlled and the fibres must be accurately aligned with the corresponding optoelectronic devices (21a-c). The fibre optics can be secured in their positions in the fibre cavities of the coupling module by any means known in the art, including mechanical locking with a bolt, snap fit, and the like, or by bonding with an adhesive.

Assembled Optoelectronic Electrode Element

The assembly of the coupling module (10) with the electronic module (20) the electrode module (40), and the optical module (30) forms an optoelectronic electrode element according to the present invention. One major concern with optoelectronic electrode elements is the size thereof, which must be as compact as possible, and at least have a similar size to an equivalent electrode element directly fed by electric leads. The compactness, but also the mechanical resistance of the optoelectronic electrode element depends also on the orientation of the optical module with respect to the electrode module. For cuff electrodes (cf. FIGS. 2&7(e)) and array electrodes it is preferred that the optical module is coupled to the electrode assembly such that the one or more fibre optics extend substantially parallel to a major axis defining the electrode module. For needle or rod electrodes (cf. FIG. 4A(d)) it is preferred that the optical module is coupled to the electrode assembly such that the one or more fibre optics extend substantially coaxially to the axis defining the needle or rod electrode module.

Figure 2B:
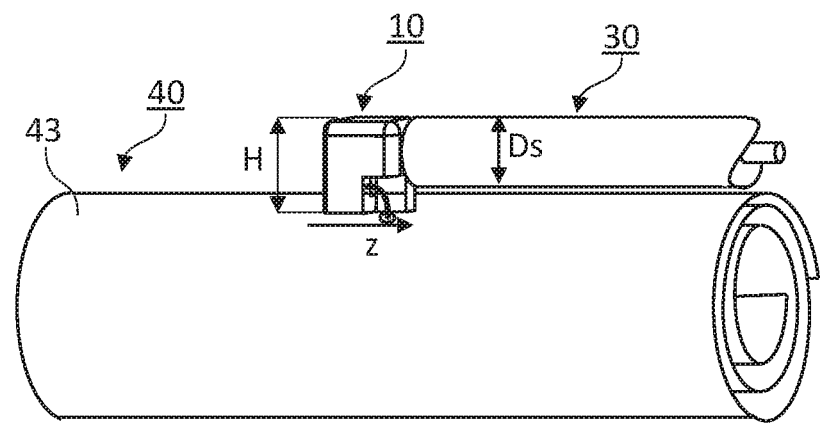

For example, for some electrode geometries including cuff electrodes, a portion of the fixing area of the electrically insulating support comprised between the first and second contact surfaces (44, 45), can be defined by a support vector, z (cf. FIG. 2). It is preferred that the feeding fibre cavity (11a) of the coupling module be substantially parallel to the support vector, z, such that, when coupled to the coupling module, the fibre optics be parallel to the support surface where they reach the coupling module. This ensures a protection of the fibre optics against any mechanical stress applied onto the element. As discussed supra, the feeding fibre optic (31a) is generally enclosed in a sheath (35) having an outer hydraulic diameter, Ds. It is preferred that the coupling module jut out of a surface of the insulating support in a first direction normal to said insulating support, by a height, H, of not more than 200%, preferably not more than 150%, more preferably not more than 100% of the hydraulic diameter, Ds, of the sheath. Such configuration is illustrated in FIG. 2(b). The same dimensional requirements may apply to a second dimension, W, normal to the first dimension, which is preferably not more than 200%, preferably not more than 150%, more preferably not more than 100% of the hydraulic diameter, Ds.

Independently of the presence of a sheath, the dimensions of the coupling element can also be defined as follows. As illustrated in FIG. 5, (a) each of the one or more fibre cavities (11a-c) of the coupling module extends substantially parallel to a support vector, z, and are all enclosed within a circle of diameter, D, normal to the support vector, z, (b) a projection of the coupling module onto a plane normal to the support vector, z, has a surface having a first dimension, H, of not more than 300%, preferably not more than 200%, more preferably not more than 100% of the diameter, D, and wherein said surface has a second dimension, W, normal to the first dimension which is preferably not more than 300%, preferably not more than 200%, more preferably not more than 100% of the diameter, D, and/or wherein (c) the first and/or second dimensions, H, W, are preferably smaller than 5 mm, more preferably smaller than 3 mm. Such dimensions of the optoelectronic electrode element of the present invention are of the same order of magnitude as the ones of traditional electrode elements.

Figure 4D:
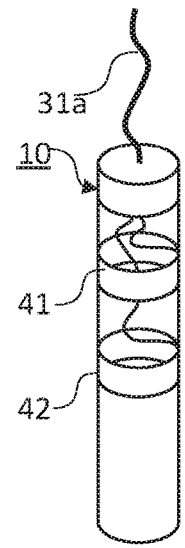
Figure 4E:
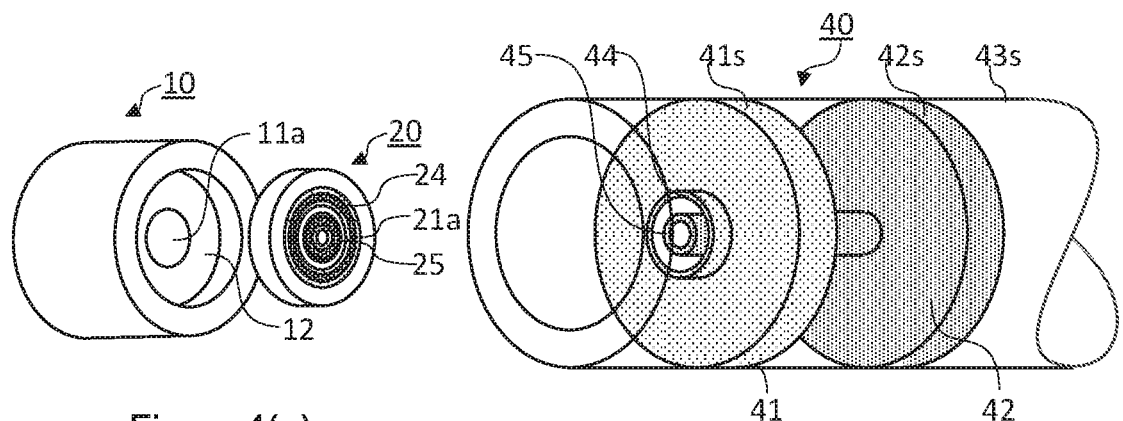
FIGS. 4(e)-4(g): show FIG. 4(e) exploded perspective views, FIG. 4(f) exploded cut views, and FIG. 4(g) assembled cut views of an alternative embodiment to the one of FIGS. 4(a)-(d), according to the present invention of modules of an optoelectronic electrode element in the form of deep brain stimulation electrodes.
Figure 4F:
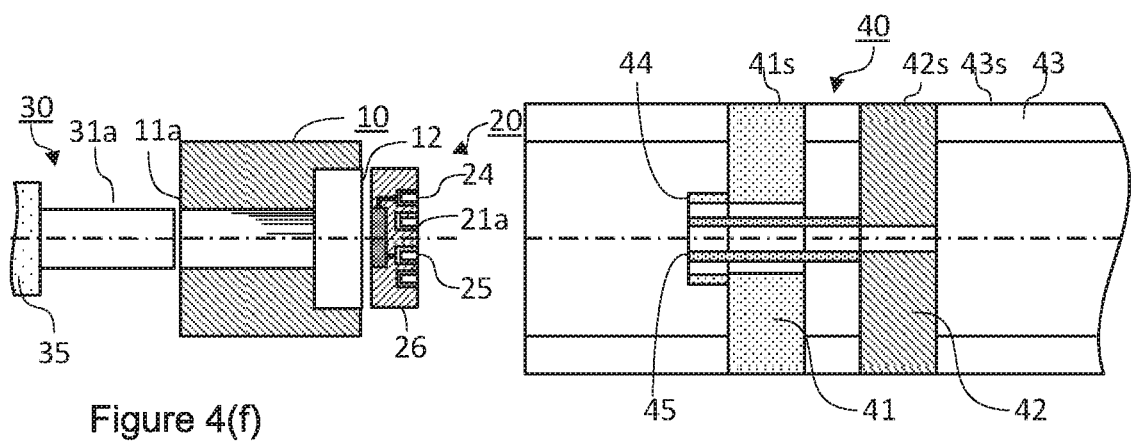
Figure 4G:
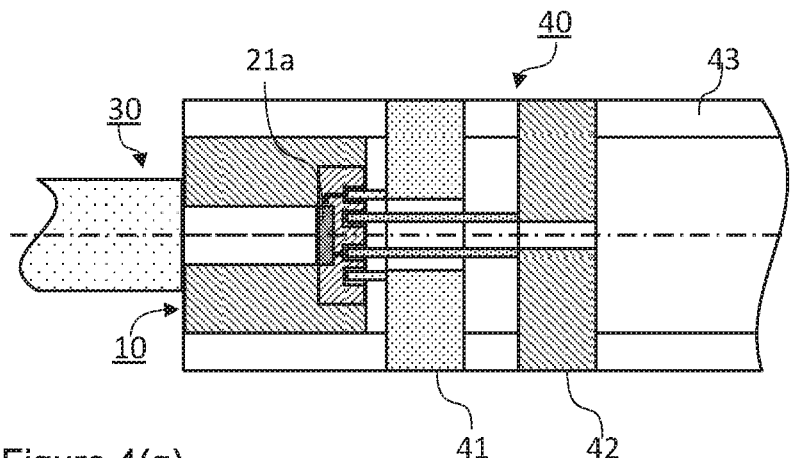

As illustrated in FIG. 7(e), the whole coupling assembly formed by the coupling module (10) and the electronic module (20), and preferably the portion of fibre optics and possibly of sheath (35) jutting out of the coupling module are embedded in an insulating polymer (60). The insulating polymer insulates and protects the interfaces between modules, as well as all electric contacts and components from ingress of pollutants and moisture present in the external environment. It also has the advantage of smoothening all external edges and corners of the optoelectronic electrode element, reducing the risks of damaging surrounding tissues, when implanted. The insulating polymer can be, for example, a silicone, an epoxy resin, an poly(p-xylylene) polymer (e.g., Parylene™), liquid crystal polymer or mixture or multi-layered laminate thereof. Applications of the optoelectronic electrode element of the present invention The first objective of the present invention is to transfer energy in the form of an optical beam emitted from a housing (50) of the IMD to an electrode module (40) in the form of electrical energy. The electrode module is located remote from the housing. In its simplest form, the housing comprises a single light source (51) controlled by a controller (4) and the optoelectronic electrode element of the present invention comprises a single feeding fibre optic (31a) coupling the single light source (51) to a single photovoltaic cell (21a) as illustrated in FIGS. 2(a), 2(b) 4(a)-(g), 6(b) and 7(a)-(e). This configuration can be used for example for the electrical stimulation of a tissue, such as a peripheral nerve, using a cuff electrode (cf. FIGS. 2(a) and (b)), or brain tissue using a deep brain stimulation electrode, as illustrated in FIG. 4(d).

In case the electrode module comprises more than a first and second electrodes, or if different sources of energy may be required by a same pair of electrodes (e.g., stimulating and recovery circuits, different wavelengths, pulse frequencies, intensities, and the like), the IMD housing (50) may comprise more than one light emitting source (51, 51R), each transmitted to the optoelectronic electrode element by a corresponding number of feeding fibre optics (31a, 31b), and optically coupled to one or more photovoltaic cells (21a, 21b). As shown in FIG. 8(b), at least an additional light source (31c) may be integrated in the stimulation and/or recovery circuits, to indicate that current is indeed flowing through a given circuit when it should.

Besides electric stimulation, an IMD can also be used for monitoring the activity of a tissue. In a first example, a tissue may create potential differences representative of the activity thereof, which are measured by the electrodes (41, 42). A light source (21c) can be provided in the optoelectronic module (20), which is powered by the energy provided by a photovoltaic cell (21a). The light energy emitted by the light source is modulated by the potential differences measured at the electrodes. The modulated light signal can be transferred to the housing (50) via a feedback fibre optic (31c) and recorded and/or interpreted by a processor lodged in said housing. This embodiment requires at least an additional light source (31c) in the optoelectronic module, and an electric connection between the light source and the photovoltaic cell. As already explained, because the amplitude of the potential differences thus measured is so low, an amplifier could be required to amplify the modulations measured by the electrodes. In that case, the optoelectronic circuit comprises a photovoltaic cell for powering an amplification and signal processing chain. Variations of electrical potential differences measured between the first and second contact surfaces of the electrode module are thus amplified, processed, and converted into a suitable light emission signal. The feedback fibre optic (31c) can be the same or different from the feeding fibre optic, depending on whether or not the light source (31c) and photovoltaic cell (31a) are arranged concentrically in the optoelectronic module.

The IMD can also be used for monitoring the activity of a tissue, using a voltage sensitive optoelectronic device. Such a transducer can be an electro-optic modulator (EOM) which is an optical device in which a signal-controlled element exhibiting the electro-optic effect is used to modulate a beam of light. The modulation may be imposed on the phase, frequency, amplitude, or polarization of the beam. A laser source is outputted at the IMD and is received by the electro-optic modulator which in turns re-emits light modulated by the electrophysiological signal.

Another example of monitoring application is by direct illumination of a tissue with the light transmitted by the feeding fibre optic (31a). The light reflected from or transmitted through said tissue may be collected and a feedback light beam can be returned to the housing via a feedback fibre optic (31c). Again, an amplification of the intensity of the reflected or transmitted light may be required before sending back the feedback light beam via the feedback fibre optic. Said amplification can be powered by the electrical energy supplied by the photovoltaic cell (31a).

Optoelectronic electrode elements according to the present invention may therefore comprise more than one feeding fibre optic (31a), more than one feedback fibre optic (31c), and/or more than one fibre optic (31b) which may act either or both as feeding and/or feedback fibre optic. A coupling module (10) suitable for receiving more than one fibre optic is illustrated in FIG. 5, and an optoelectronic module (20) suitable for establishing a continuous energy transfer chain through all of the more than one fibre optics is illustrated in FIGS. 5 and 6(a).

A sealed optoelectronic electrode element wherein the optoelectronic circuit, which is most sensitive to aggression from biological fluids when implanted, can be obtained, by isolating the circuit cavity from the ambient atmosphere, by sealing the circuit cavity with a lid (28, 29), the fibre optics cavities with a window (18), and any fluid communication through a wall by using vias (22).

| REF# | Feature |
|---|---|
| 4 | Controller of light source 51 |
| 4R | Controller of light source 51R |
| 10 | Coupling module |
| 11a | Cavity for feeding fibre optic (31a) |
| 11b | Cavity for fibre optic (31b) |
| 11c | Cavity for fibre optic (31c) |
| 12 | circuit receiving portion |
| 14 | Opening for establishing electric contact between $1^{st}$ optoelectronic module contact surface and $1^{st}$ coupling surface |
| 15 | Opening for establishing electric contact between $2^{nd}$ optoelectronic module contact surface and $2^{nd}$ coupling surface |
| 16 | Electric wire bringing in electric contact $1^{st}\&2^{nd}$ optoelectronic module contact surfaces with $1^{st}\&2^{nd}$ coupling surfaces |
| 16c | Electrically conducting paste bringing in electric contact $1^{st}\&2^{nd}$ optoelectronic module contact surfaces with $1^{st}\&2^{nd}$ coupling surfaces |
| 16w | Coupling means of electric wire with $1^{st}\&2^{nd}$ coupling surfaces |
| 18 | Window |
| 20 | Optoelectronic module |
| 21a | Photovoltaic cell |
| 21b | Photovoltaic cell or light source |

-continued

| REF# | Feature |
|---|---|
| 21c | Light source (e.g., LED) in optoelectronic circuit |
| 22 | Via |
| 23 | Conductive layer coated over via's ends |
| 24 | $1^{st}$ optoelectronic module contact surface |
| 25 | $2^{nd}$ optoelectronic module contact surface |
| 26 | Electric contact between electronic circuit and $1^{st}\&2^{nd}$ optoelectronic module contact surfaces |
| 26w | Coupling means of electric wire with $1^{st}\&2^{nd}$ optoelectronic module contact surfaces |
| 27 | Sealing polymer of the optoelectronic module |
| 28 | Support board |
| 29 | Main board |
| 30 | Optical transmission module |
| 31a | Feeding fibre optic |
| 31b | Feeding fibre optic or feedback fibre optic |
| 31c | Feedback fibre optic |
| 35 | Sheath |
| 40 | Electrode module |
| 41 | First electrode |
| 41s | First electrode surface |
| 42 | Second electrode |
| 42s | Second electrode surface |
| 43 | Electrically insulating support |
| 43s | Electrode coupling surface |
| 44 | First coupling surface |
| 45 | Second coupling surface |
| 46 | Electric contact between $1^{st}\&2^{nd}$ electrode surfaces and $1^{st}\&2^{nd}$ coupling surfaces |
| 50 | IMD housing |
| 51 | First light source in housing |
| 51R | Second light source in housing |

The invention claimed is:

1. An optoelectronic electrode element which is adapted to be implantable in a human or animal body for placement on a biological tissue for at least one of electrically stimulating or sensing physiological parameters of said biological tissue, said optoelectronic electrode element comprising:
    an electrode module (40) comprising:
        an electrically insulating support (43) for coupling the implantable electrode element to a biological tissue, wherein said electrically insulating support comprises an electrode coupling surface (43s) and wherein the electrically insulating support partly embeds:
        at least a first electrode (41) comprising a first electrode surface (41s) and a second electrode (42) comprising a second electrode surface (42s), the at least first and second electrodes being separated from one another and exposed to ambient atmosphere at the respective first and second electrode surfaces, such that when the optoelectronic electrode element is coupled to a biological tissue, the first and second electrode surfaces (41s, 42s) are in electrical contact with the biological tissue, and
        first and second coupling surfaces (44, 45) in electrical communication with the first and second electrodes (41, 42), respectively;
    an optoelectronic module (20) comprising an optoelectronic circuit including one or more optoelectronic devices (21a-c) suitable for transforming optical energy into one or more of electrical energy or electrical energy into optical energy, said optoelectronic module further comprising a first and second optoelectronic module contact surfaces (24, 25) in electrical communication with the optoelectronic circuit;
    an optical module (30) comprising one or more fibre optics (31a-c), each having a distal end characterized by a cross-section of hydraulic diameter, Dh, said distal end being in optical communication with a corresponding optoelectronic device;

a coupling module (10) comprising:
  a circuit receiving portion (12) for inserting, positioning, and rigidly fixing the optoelectronic module (20) to the coupling module (10);
  one or more fibre cavities (11a-c), each of the one or more fibre cavities being configured for inserting and coupling the distal end of a corresponding fibre optic of the one or more fibre optics (31a-c) such that the cross-section of the distal end is in optical communication with, and faces in accurate alignment with the corresponding optoelectronic device; and
  wherein, the coupling module (10) is coupled directly to a fixing area of the electrically insulating support (43), and wherein the first and second optoelectronic module contact surfaces (24, 25) are distinct from and in electrical contact with the first and second coupling surfaces (44, 45) of the electrode module, respectively.

2. The optoelectronic electrode element according to claim 1, wherein, each of the one or more fibre cavities (11a-c) of the coupling module extends substantially parallel to a support vector, z, and are all enclosed within a circle of diameter, D, normal to the support vector, z, wherein at least one of:
  a projection of the coupling module onto a plane normal to the support vector, z, has a surface having a first dimension, H, of not more than 300%, of the diameter, D, and wherein said surface has a second dimension, W, normal to the first dimension which is not more than 300% of the diameter, D, or;
  at least one of the first or second dimensions, H, W, are smaller than 5 mm.

3. The optoelectronic electrode element according to claim 1, wherein the one or more optoelectronic devices comprise a photovoltaic cell, whose corresponding fibre optic is a feeding fibre optic (31a); and
  wherein the first and second optoelectronic module contact surfaces (24, 25) are in electrical communication with and electrically fed by the photovoltaic cell.

4. The optoelectronic electrode element according to claim 1, wherein the one or more optoelectronic devices comprise a light emitting device (21c), whose corresponding fibre optic is a feedback fibre optic (31c), said light emitting device having an optical output which is at least one of:
  can be modulated by variations of an electrical potential difference between the first and second electrode surfaces of the electrode module or
  is representative of activity of an optoelectronic device suitable for transforming optical energy into electrical energy.

5. The optoelectronic electrode element according to claim 4, wherein the electronic circuit comprises an amplification chain for amplifying the variations of the electrical potential difference between the first and second electrode surfaces of the electrode module, said amplification chain being powered by a photovoltaic cell (21a, 21b) of the optoelectronic module.

6. The optoelectronic electrode element according to claim 1, wherein the first and second optoelectronic module contact surfaces (24, 25) are in electrical communication with the first and second coupling surfaces (44, 45) of the electrode module, respectively, by electrically bridging the first and second optoelectronic module contact surfaces with the first and second coupling surfaces of the electrode module by means of one or more of;

a conductive paste (16c) comprising a conductive polymer or a polymer loaded with conductive particles;

a conductor (16) selected among a conductive wire or ribbon, a printed circuit or track, wherein said conductor is bonded at a first end to the first or second optoelectronic module contact surface (24, 25) and, at a second end to the corresponding first or second coupling surface (44, 45), wherein bonding can be formed by one or more of wire bonding, ribbon bonding, wire or ribbon laser welding, soldering; or direct contact of the first or second optoelectronic module contact surface (24, 25) with the corresponding first or second coupling surface (44, 45), and welding, riveting, clamping, snap fitting, with a plug and socket assembly, soldering with a conductive soldering material the surfaces in contact, or by simple contact between planar surfaces.

7. The optoelectronic electrode element according to claim 1, wherein the whole coupling module is embedded in an insulating polymer (60), for at least one of stabilizing the coupling module on the insulating support, or for insulating the coupling module from the surrounding environment.

8. The optoelectronic electrode element according to claim 7, wherein the one or more fibre optics, excluding the distal ends thereof, are enclosed in a sheath (35); and
  wherein the insulating polymer continuously embeds the distal ends and part of the sheath.

9. The optoelectronic electrode element according to claim 7, wherein the insulating polymer (60) is formed of at least one of silicone, an epoxy resin, a poly(p-xylylene) polymer, liquid crystal polymer or mixture or multi-layered laminate thereof.

10. The optoelectronic electrode element according to claim 1, wherein each of the one or more optoelectronic devices (21a-c) is separated from the distal end of the corresponding fibre optic (31a-c) by a corresponding window (18) transparent to wavelengths transmitted to or from the corresponding fibre optic.

11. The optoelectronic electrode element according to claim 10, wherein the corresponding windows are an integral part of the coupling module; and
  wherein the coupling module is made of a transparent ceramic material forming a monolithic block including the corresponding windows.

12. The optoelectronic electrode element according to claim 11, wherein the transparent ceramic material is formed of fused silica, borosilicate, spinel, sapphire, or yttrium oxide.

13. The optoelectronic electrode element according to claim 1, wherein:
  the circuit receiving portion (12) is formed by a circuit cavity;
  the optoelectronic circuit is supported on a support board (28) defining a support board perimeter mating or overlapping the circuit cavity;
  the optoelectronic module is inserted in or over the circuit cavity forming a support interfacial perimeter between the support board perimeter and the coupling module; and
  the support interfacial perimeter is sealed with a sealing element applied to the coupling module.

14. The optoelectronic electrode element according to claim 1, wherein:
  the circuit receiving portion (12) is formed by a circuit cavity;

the optoelectronic circuit is supported on a support board (28) defining a support board perimeter mating or smaller than the circuit cavity;

the support board is coupled to a first surface of a main board (29), defining a main board perimeter, mating or overlapping the circuit cavity;

the optoelectronic module is inserted in or over the circuit cavity forming a main interfacial perimeter between the main board perimeter and the coupling module;

the main interfacial perimeter is sealed with a sealing element selected among a welding or soldering line, or a sealing polymer (27) applied to the main interfacial perimeter; and wherein the first and second optoelectronic module contact surfaces (24, 25) are located on a second surface of the main board, separated from the first surface of the main board; and wherein the electrical communication between the optoelectronic circuit and the first and second optoelectronic module contact surfaces (24, 25) is ensured by vias, extending across the thickness from the first to the second surface of the main board.

15. The optoelectronic electrode element according to claim 14, wherein the sealing element is a welding or soldering line, or a sealing polymer (27).

16. The optoelectronic electrode element according to claim 1, wherein the one or more optoelectronic devices comprise:

a first photovoltaic cell (21*a*), whose corresponding fibre optic is a first feeding fibre optic (31*a*), wherein said first photovoltaic cell is arranged for feeding electrical power to a stimulating circuit including the first and second electrodes, for transporting charges in a first direction to stimulate a tissue;

a second photovoltaic cell (21*b*), whose corresponding fibre optic is a second feeding fibre optic (31*b*), which can be the same as or different from the first feeding fibre optic (31*a*), wherein said second photovoltaic cell is arranged for feeding electrical power to a recovery circuit including the first and second electrodes, for transporting charges in a second direction, opposite the first direction, to balance the charges delivered by the stimulation circuit; and one or more sources of light, including a LED or a laser diode included in at least one of the stimulation circuit or the recovery circuit, whose corresponding fibre optics are one or more feedback fibre optics (31*c*), wherein said one or more sources of light are powered by at least one of the first or second photovoltaic cells, and whose output is optionally modulated by variations of an electrical potential measured between the first and second electrodes.

17. The optoelectronic electrode element according to claim 1, wherein the optoelectronic circuit is sealed from ambient atmosphere by one or more of the following:

the optoelectronic circuit is enclosed in a circuit cavity provided in the coupling module, and an interface formed between the optoelectronic module and the coupling module is sealed by a sealing element;

the one or more fibre cavities are closed at one end by a window (18) transparent to wavelengths transported through the fibre optics, and separating the fibre cavities from the circuit cavity; or all electrical communications between a first surface and a second surface of a wall of a non-conductive component is formed by vias made of at least one of conductive metals extending from the first to the second surfaces of the wall, or a coating of conductive metal is applied over the vias where they reach the first and second surfaces.

18. An implantable medical device comprising:

a housing comprising one or more sources of light (51, 51R) and a controller (4, 4R); and an optoelectronic electrode element according to claim 1 comprising one or more photovoltaic cells (21*a*, 21*b*), and one or more corresponding fibre optics (31*a*, 31*b*);

wherein the one or more sources of light of the housing are in optical communication with the one or more photovoltaic cells through the one or more fibre optics; and wherein the electrode module is shaped as a cuff or helical ribbon suitable for being fitted around a nerve, a needle or rod suitable for being inserted in a brain tissue, a two-dimensional array suitable for being laid over the cerebral cortex or on the spinal cord.

* * * * *